(12) United States Patent
Ali et al.

(10) Patent No.: US 11,573,191 B2
(45) Date of Patent: Feb. 7, 2023

(54) MEASURING GAS IN SHALE RESERVOIRS

(71) Applicant: W. D. Von Gonten Laboratories, LLC, Houston, TX (US)

(72) Inventors: Safdar Ali, Houston, TX (US); Ashish Mathur, Houston, TX (US); Chad Belanger, Houston, TX (US)

(73) Assignee: W. D. Von Gonten Laboratories, LLC

( * ) Notice: Subject to any disclaimer, the term of this patent is extended or adjusted under 35 U.S.C. 154(b) by 0 days.

(21) Appl. No.: 17/168,552

(22) Filed: Feb. 5, 2021

(65) Prior Publication Data

US 2021/0239632 A1 Aug. 5, 2021

Related U.S. Application Data

(60) Provisional application No. 62/970,262, filed on Feb. 5, 2020.

(51) Int. Cl.
*G01N 24/08* (2006.01)
*G01N 33/24* (2006.01)
*G01R 33/46* (2006.01)
*G01R 33/31* (2006.01)
*G01R 33/30* (2006.01)

(52) U.S. Cl.
CPC .......... *G01N 24/081* (2013.01); *G01N 33/24* (2013.01); *G01R 33/305* (2013.01); *G01R 33/31* (2013.01); *G01R 33/4633* (2013.01)

(58) Field of Classification Search
CPC .... G01N 24/081; G01N 33/24; G01R 33/305; G01R 33/31; G01R 33/4633; G01R 33/448
See application file for complete search history.

(56) References Cited

U.S. PATENT DOCUMENTS 9,720,124 B2 * 8/2017 Kadayam Viswanathan ............... G01V 3/38
2004/0008027 A1 * 1/2004 Prammer .................. G01V 3/32
702/6

* cited by examiner

*Primary Examiner* — Susan S Lee
(74) *Attorney, Agent, or Firm* — Derek Forinash; Porter Hedges LLP

(57) ABSTRACT

Methods for determining a volume of stored gas within a rock sample includes loading a rock sample into an overburden cell. A hydrocarbon gas at a gas pressure is applied to the rock sample and a confining fluid at a confining pressure is applied to the overburden cell. The confining pressure and the gas pressure are increased until a first pressure and temperature condition is met. With the rock sample maintained at the first temperature and pressure condition, a nuclear magnetic resonance spectrometer is used to scan the rock sample and measure a hydrocarbon gas volume within the rock sample. This measured hydrocarbon gas volume is then corrected using a Real Gas Index to determine the volume of stored gas within the rock sample.

20 Claims, 1 Drawing Sheet

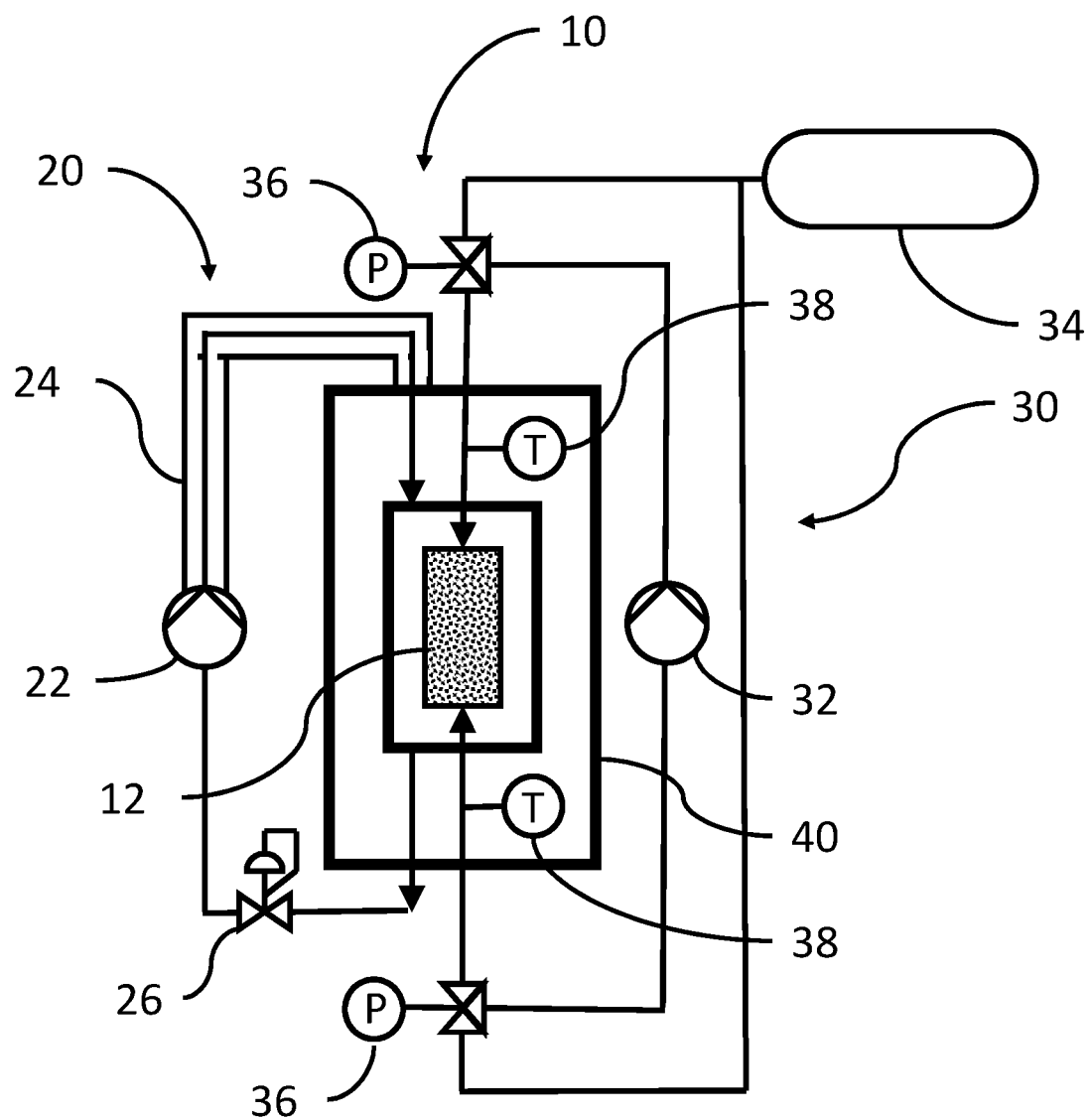

MEASURING GAS IN SHALE RESERVOIRS

CROSS-REFERENCE TO RELATED APPLICATIONS

This application claims the benefit of U.S. patent application Ser. No. 62/970,262, filed Feb. 5, 2020 and incorporated herein by reference.

BACKGROUND

The determination of the gas-in-place for shale gas reservoirs is important for assessing the quality of the reservoir and the suitability of that reservoir for development. Generally, gas-in-place for shale gas reservoirs is estimated by partitioning the total stored gas into free and adsorbed gas. Free gas is gas that is present in the reservoir either in gaseous phase at reservoir pressures or that will evolve out of the formation fluid as the formation pressure decreases. The free gas volume is calculated using the porosity of the rock and the amount of gas that can be stored in the rock at a given pressure and temperature assuming 'real gas' behavior.

Adsorbed gas is gas that accumulates on the pore surfaces of solid materials in the formation. The volume of adsorbed gas is computed from Langmuir adsorption isotherm tests, which assume a mono-layer adsorption of gas (of higher density) on the pore surfaces. The free gas and adsorbed gas volumes make up the total gas available in the reservoir but are assumed to behave differently under pressure drawdown scenarios.

It is understood that the physical properties and behavior of fluids in confined pore spaces are very different than bulk fluid behavior. In nano-porous rock systems, characteristic length scale of the medium approaches both the mean free path and the molecular size of the saturating fluid. Thus, in these systems fluid-pore interactions may tend to dominate over fluid-fluid interactions. For example, heightened capillary forces may impact interfacial tensions, fluid densities, viscosities, saturation pressures, phase compositions, and phase boundaries.

Understanding the behavior of gas stored in nano-porous rock systems is important for predicting and managing production from shale gas reservoirs. Thus, there remains a need for experimental methods for evaluating the behavior of gas stored in nano-porous rock systems.

BRIEF DESCRIPTION OF THE DRAWINGS

For a more detailed description of the embodiments of the disclosure, reference will now be made to the accompanying drawings, wherein:

FIG. 1 illustrates one embodiment of the current invention.

DETAILED DESCRIPTION

It is to be understood that the following disclosure describes several exemplary embodiments for implementing different features, structures, or functions of the invention. Exemplary embodiments of components, arrangements, and configurations are described below to simplify the disclosure; however, these exemplary embodiments are provided merely as examples and are not intended to limit the scope of the invention. Additionally, the disclosure may repeat reference numerals and/or letters in the various exemplary embodiments and across the FIGURES provided herein. This repetition is for the purpose of simplicity and clarity and does not in itself dictate a relationship between the various exemplary embodiments and/or configurations discussed in the various FIGURES. Finally, the exemplary embodiments presented below may be combined in any combination of ways, i.e., any element from one exemplary embodiment may be used in any other exemplary embodiment, without departing from the scope of the disclosure.

All numerical values in this disclosure may be exact or approximate values unless otherwise specifically stated. Accordingly, various embodiments of the disclosure may deviate from the numbers, values, and ranges disclosed herein without departing from the intended scope. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

In the following discussion and in the claims, the terms "including" and "comprising" are used in an open-ended fashion, and thus should be interpreted to mean "including, but not limited to." Furthermore, as it is used in the claims or specification, the term "or" is intended to encompass both exclusive and inclusive cases, i.e., "A or B" is intended to be synonymous with "at least one of A and B," unless otherwise expressly specified herein.

Certain terms are throughout the following description and claims refer to particular components. As one having ordinary skill in the art will appreciate, various entities may refer to the same component by different names, and as such, the naming convention for the elements described herein is not intended to limit the scope of the invention, unless otherwise specifically defined herein. Further, the naming convention used herein is not intended to distinguish between components that differ in name but not function.

Referring now to FIG. 1, a system 10 for testing a rock sample 12 comprises an overburden system 20, a gas injection system 30, and a nuclear magnetic resonance (NMR) spectrometer 40. Overburden system 20 includes a fluid pump 22, heater 24, pressure regulator 26, and overburden cell 28. Overburden cell 28 may be constructed from a ceramic or other material that does not generate an NMR signal. Gas injection system 30 includes a vacuum pump 32, gas source 34, pressure gauges 36, and thermocouples 38. NMR spectrometer 40 may be a 12 MHz NMR spectrometer capable of performing gradient measurements in 1D, 2D, or 3D.

Referring still to FIG. 1, a rock sample 12 is loaded into overburden cell 28 that is placed in the NMR spectrometer 40. Overburden cell 28 is coupled to the overburden system 20 and the sample 12 is coupled to the gas injection system 30. Confining pressure is applied to the overburden cell 28 by using fluid pump 22 to pressurize a confining fluid that may also be heated. The confining fluid is preferably a non-reactive fluid that does not produce an NMR signal, such as Flourinert™ sold by 3M™. In certain test procedures, the sample 12 may be subjected to the temperatures and pressures typical in the formation from which the sample was taken.

Vacuum pump 32 is used to draw hydrocarbon gas from gas source 34 to the sample 12 at controlled pressures, which may be between 100 psi and 10000 psi to saturate the sample with hydrocarbon gas by injecting gas from both sides of the sample 12. Gas pressures in the sample are constantly monitored above and below the sample using high precision pressure gauges till pressures stabilize, conveying complete saturation at a given pressure. During this saturation process, overburden system 20 can be used to control the desired confining pressure and temperature of the sample 50. As the sample 12 is saturated with hydrocarbon gas, NMR spectrometer 40 is used to measure the amount of hydrocarbon gas being stored within the sample 12 at the gradually increasing pressures and temperatures.

In certain embodiments, NMR 1D, 2D and 3D scans are performed during the saturation process so as to measure the amount of gas stored and compute the density of the gas within the sample 12 at different pressures. As the injection pressure is increased, confining pressure may be kept about a 1000-2000 psi higher than the injection pressure until reservoir pressures are reached. To regulate the confining pressure, a back-pressure regulator 26 (set at reservoir overburden stress) is used which discharges the extra confining fluid back to the confining fluid pump 22 as needed.

To heat the sample and the gas in the sample, heater system 24 is used. Confining pump 22 is flowed at high flow rates (25 cc/min) in the overburden cell 28. The confining lines connecting the pump 22 to the overburden cell 28 are heated using heater system 24. This flow loop heats the confining fluid which in turn heats the sample 12 and the gas stored in the sample. Inline thermocouples 38 are used to monitor the temperatures at the top and bottom of the sample 12. NMR 1D, 2D and 3D scans are performed at reservoir temperature and pressure to understand gas storage in the samples.

To establish known behavior of a hydrocarbon gas in conventional large pore systems, and the associated NMR magnetization signal, a machinable glass ceramic cylindrical plug with a cylindrical bore of a known volume can be used as a standard. This standard has a fixed void volume associated with the cylindrical bore and this volume can be measured in multiple ways (helium porosimetry, calipered dimensions, Archimedes immersion, etc). The standard void volume becomes the reference for the measured NMR magnetization signal of a gas that is stored in this volume at a given temperature and pressure when the gas is behaving as a 'real gas' without the influence of any nano-pore confinement effects.

The ratio of the measured NMR volume of the standard to the true void volume of the standard can be defined as the "Real Gas Index" for a particular hydrocarbon gas for a range of pressures and temperatures. When the same hydrocarbon gas is stored in porous media at a given pressure and temperature, the deviation of the measured NMR volume from the Real Gas Index for that porous media sample would indicate that the gas is not behaving as a 'real gas' in the porous media.

By way of example, this test was performed on a known conventional pore size rock system (Berea sandstone-average pore size of about 10 to 20 microns) and the measured NMR response indicated that gas in this rock behaves purely as a 'real gas.' The gas indexes for the standard and Berea sandstone were also in agreement with published NIST (National Institute of Standards and Technology) density values. Further, the difference between the NMR Real Gas Index and the actual NMR magnetization of the gas in the porous media can be used to estimate the difference in the density of the gas due to pore confinement effects.

For the gas storage measurement, NMR hydrocarbon gas volumes at reservoir temperature and pressure are measured based using 2D NMR T1T2 maps. These NMR volumes are then corrected using the Real Gas Index measured on the standard at the same temperature and pressure. These corrected hydrocarbon gas volumes can then be compared to the void volumes measured using helium porosimetry to further understand and quantify pore confinement effects.

Thus, experimentation using the described methods allow for the measurement of density of supercritical hydrocarbon gases, calculation of total gas-in-place, and establishment of gas saturation levels in nano-pore dominated systems of organic shale rocks at varying pressures and temperatures (reservoir conditions). The methods described herein can support the quantification of hydrocarbon gas storage in nano-pore organic shales using NMR relaxometry to understand phase behavior of hydrocarbon gas as a function of capillary condensation and pore-confinement and measure mass transport of stored gas in nano-pore rock systems as reservoir pressure is dropped (drawdown); while keeping temperature and overburden stress at reservoir conditions.

While the disclosure is susceptible to various modifications and alternative forms, specific embodiments thereof are shown by way of example in the drawings and description. It should be understood, however, that the drawings and detailed description thereto are not intended to limit the claims to the particular form disclosed, but on the contrary, the intention is to cover all modifications, equivalents, and alternatives falling within the scope of the claims.

What is claimed is:

1. A method for determining a volume of stored gas comprising:
   loading a rock sample into an overburden cell;
   supplying a hydrocarbon gas at a gas pressure to the rock sample;
   supplying a confining fluid at a confining pressure to the overburden cell;
   increasing the confining pressure and the gas pressure until a first condition is met;
   scanning the rock sample with a nuclear magnetic resonance spectrometer to measure a hydrocarbon gas volume within the rock sample; and
   determining a volume of stored gas within the rock sample by using a Real Gas Index to correct the measured hydrocarbon gas volume.

2. The method of claim 1, wherein the rock sample is at reservoir temperature and reservoir pressure in the first condition.

3. The method of claim 1, wherein the hydrocarbon gas volume is measured using 2D T1T2 maps.

4. The method of claim 1, further comprising performing 1D, 2D, and 3D scans with the nuclear magnetic resonance spectrometer while the rock sample is at reservoir temperature and reservoir pressure.

5. The method of claim 1, wherein the Real Gas Index is the ratio of a gas volume as measured by the nuclear magnetic response spectrometer and a measured void volume at a selected temperature and pressure.

6. The method of claim 1, wherein the overburden cell is constructed from a material that does not produce a nuclear magnetic resonance signal.

7. The method of claim 1, wherein the confining fluid is a material that does not produce a nuclear magnetic resonance signal.

8. The method of claim 1, wherein the nuclear magnetic resonance spectrometer operates at 12 MHz.

9. A method for measuring stored gas comprising:
   loading a rock sample into an overburden cell;
   supplying a hydrocarbon gas at a gas pressure to the rock sample;
   supplying a confining fluid at a confining pressure to the overburden cell;

increasing the confining pressure and the gas pressure until the rock sample is at reservoir temperature and reservoir pressure;

maintaining the rock sample at reservoir temperature and reservoir pressure until the rock sample is saturated with the hydrocarbon gas;

scanning the rock sample with a nuclear magnetic resonance spectrometer to measure a hydrocarbon gas volume within the rock sample; and determining a volume of stored gas within the rock sample by using a Real Gas Index to correct the measured hydrocarbon gas volume.

10. The method of claim 9, wherein the rock sample is scanned with the nuclear magnetic resonance spectrometer to determine if the rock sample is saturated with the hydrocarbon gas.

11. The method of claim 9, wherein the hydrocarbon gas volume is measured using 2D T1T2 maps generated from data obtained by the nuclear magnetic resonance spectrometer.

12. The method of claim 9, further comprising performing 1D, 2D, and 3D scans with the nuclear magnetic resonance spectrometer while the rock sample is at reservoir temperature and reservoir pressure.

13. The method of claim 9, wherein the Real Gas Index is the ratio of a gas volume as measured by the nuclear magnetic response spectrometer and a measured void volume at a selected temperature and pressure.

14. The method of claim 9, wherein the overburden cell is constructed from a material that does not produce a nuclear magnetic resonance signal.

15. The method of claim 9, wherein the confining fluid is a material that does not produce a nuclear magnetic resonance signal.

16. The method of claim 9, wherein the nuclear magnetic resonance spectrometer operates at 12 MHz.

17. A method for measuring stored gas comprising:

loading a standard sample into an overburden cell, wherein the standard sample has a known void volume;

supplying a hydrocarbon gas at a gas pressure to the standard sample;

supplying a confining fluid at a confining pressure to the overburden cell;

increasing the confining pressure and the gas pressure until the standard sample is at selected temperature and pressure;

maintaining the standard sample at the selected temperature and pressure until the standard sample is saturated with the hydrocarbon gas;

scanning the standard sample with a nuclear magnetic resonance spectrometer to measure a hydrocarbon gas volume within the standard sample;

dividing the measured hydrocarbon gas volume in the standard sample by the known void volume of the standard sample to determine a Real Gas Index at the selected temperature and pressure;

loading a rock sample into the overburden cell;

increasing the confining pressure and the gas pressure until the rock sample is at the selected temperature and pressure;

maintaining the rock sample at the selected temperature and pressure until the rock sample is saturated with the hydrocarbon gas;

scanning the rock sample with a nuclear magnetic resonance spectrometer to measure a hydrocarbon gas volume within the rock sample; and determining a volume of stored gas within the rock sample by using the Real Gas Index to correct the measured hydrocarbon gas volume.

18. The method of claim 17, wherein the hydrocarbon gas volume is measured using 2D T1T2 maps generated from data obtained by the nuclear magnetic resonance spectrometer.

19. The method of claim 17, wherein the overburden cell and the confining fluid do not produce a nuclear magnetic resonance signal.

20. The method of claim 17, wherein the nuclear magnetic resonance spectrometer operates at 12 MHz.

* * * * *